United States Patent [19]
Kelzer

[11] Patent Number: 5,184,517
[45] Date of Patent: Feb. 9, 1993

[54] PRINTED CIRCUIT BOARD TEST FIXTURE AND METHOD

[76] Inventor: Robert Kelzer, 2111 E. Pinetree Blvd., Thomasville, Ga. 31792

[21] Appl. No.: 786,303
[22] Filed: Nov. 1, 1991
[51] Int. Cl.$^5$ ............................................. G01N 3/20
[52] U.S. Cl. .................................................. 73/851
[58] Field of Search ................. 73/851, 849, 812, 850

[56] References Cited

U.S. PATENT DOCUMENTS 4,358,962 11/1982 Ashby ................................... 73/849
4,763,529 8/1988 Leonard et al. ................... 73/851 X

*Primary Examiner*—Jerry W. Myracle
*Attorney, Agent, or Firm*—Jones, Askew & Lunsford

[57] ABSTRACT

There is disclosed a printed circuit board text fixture and method for testing printed circuit boards. The test fixture and test method is designed to establish statistical information concerning the breaking force for and deflection of a printed circuit board when the printed circuit board is broken along pre-existing score lines. In particular, the test fixture comprises a support surface for the circuit board to be tested, a clamp for holding the circuit board in place, an alignment target for locating the score line on the circuit board with respect to the clamp, a force gauge for exerting and measuring a downward force on the circuit board until the circuit board breaks along the score line, and a travel indicator for indicating the maximum flex experienced by the circuit board just prior to breaking.

2 Claims, 2 Drawing Sheets

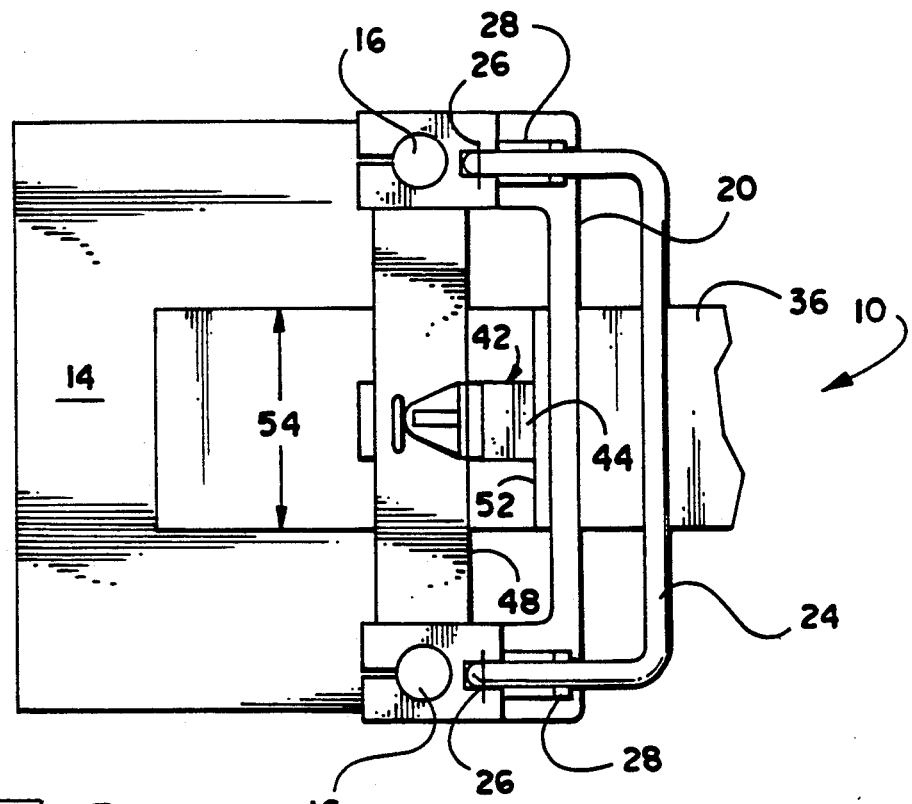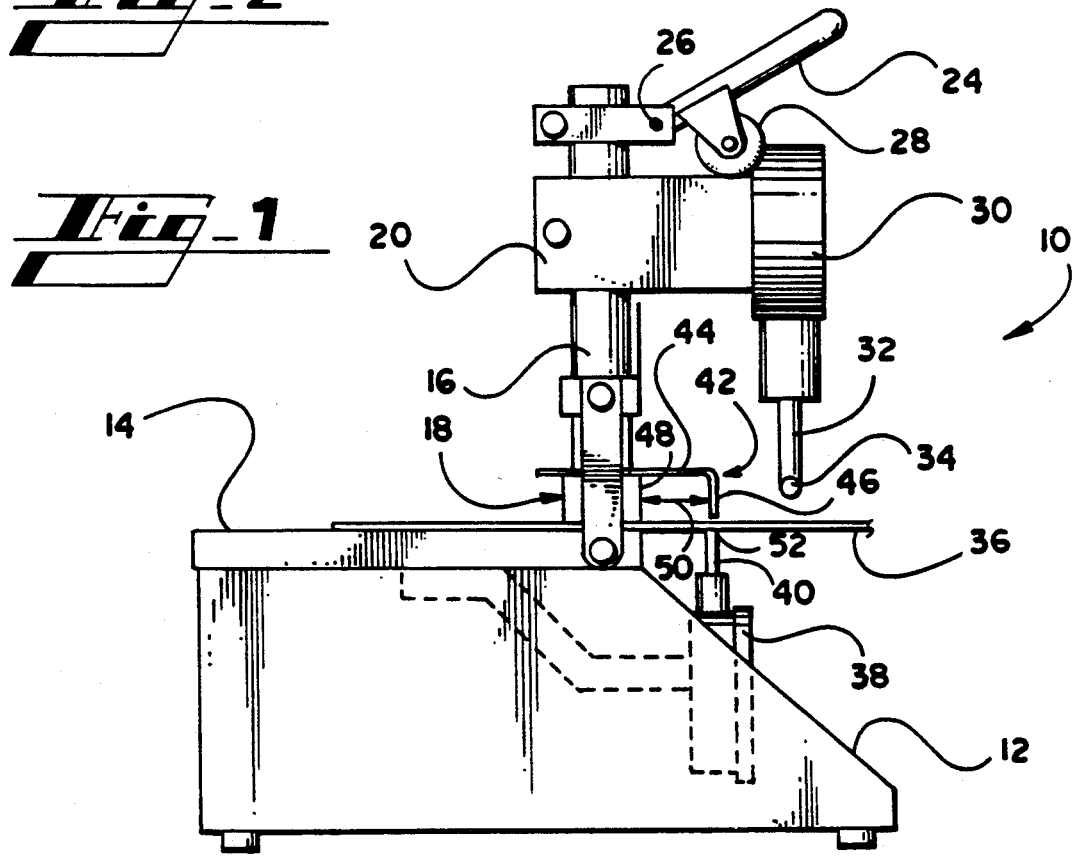

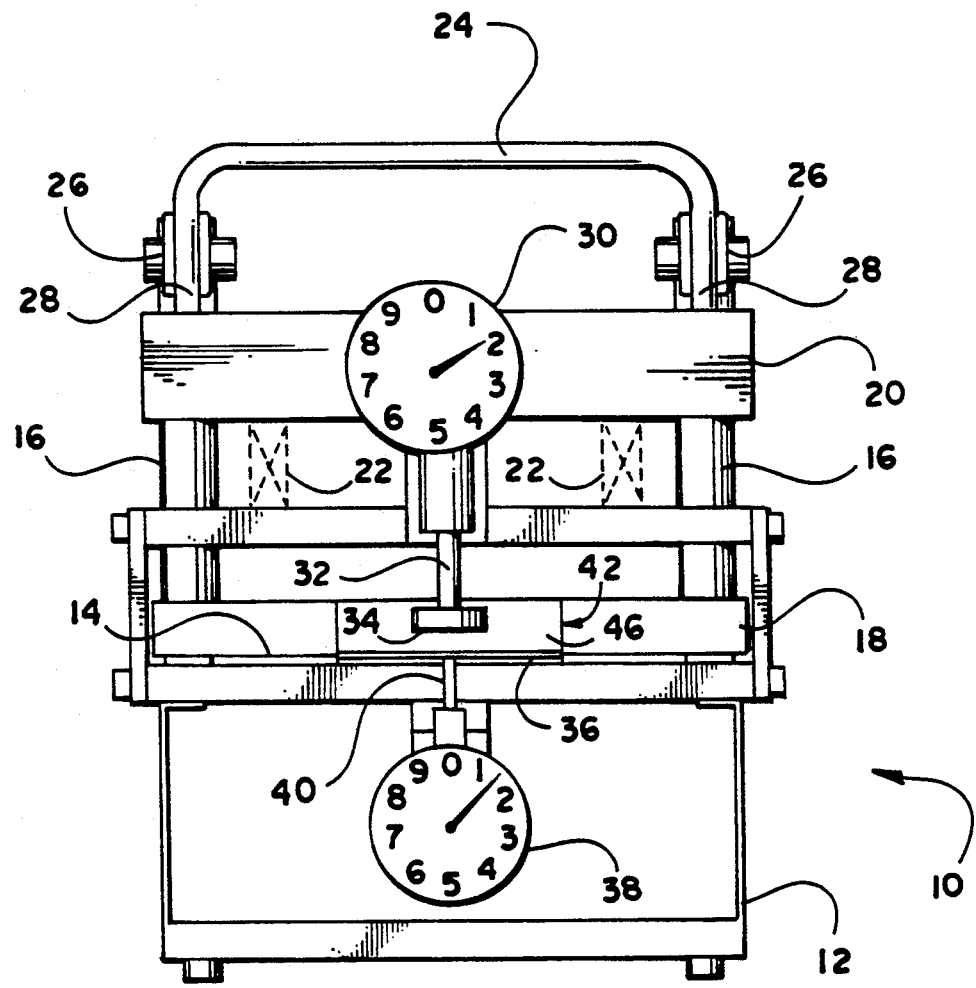
Fig_3

PRINTED CIRCUIT BOARD TEST FIXTURE AND METHOD

BACKGROUND OF THE INVENTION

This invention relates generally to testing printed circuit boards and more particularly concerns a fixture and test method for measuring the force and deflection required for breaking apart printed circuit boards along a pre-existing score line.

In manufacturing electronic equipment, manufacturers in an effort to save labor costs, have adopted automated machinery that inserts electric components into printed circuit boards. As the sophistication and capital costs of such automatic component insertion machines increase, it is important that those machines be utilized at maximum efficiency. Particularly, the efficiency of such machines can be increased if the machine can process a small number of large printed circuit boards instead of processing a larger number of small printed circuit boards. Such increase in efficiency results from eliminating some of the lost time that occurs while loading the printed circuit board without components into the machine and removing the printed circuit board with components from the machine.

In order to maximize the size of the printed circuit boards being processed, a single large printed circuit board can be provided with the circuitry and space for number of smaller circuit boards thereon. Once the components have been inserted by the automatic insertion machine, the large printed circuit board is separated into the several small circuit boards. In order to separate the larger circuit board into smaller circuit boards after the parts have been inserted, score lines are cut on the large printed circuit board before the components are inserted so that the large printed circuit board can be broken apart and separated along the previously cut score lines.

In order to assure consist and clean breakage of the printed circuit boards along the score lines, it is necessary that the board material (the web) between the score lines provided on each side of the board be of uniform thickness. U.S. Pat. No. 4,856,400 in the name of the applicant herein, discloses a particularly advantageous scoring cutter which provides a uniform depth score lines and a uniform thickness web along which the printed circuit board can be broken.

In the assembly of circuit components on printed circuit boards, the circuit boards must be held in a precise location during machine assembly and soldering. When the process is finished, the boards must break apart without excessive flex which would cause the soldered components to break or lift from the soldered paths. At the same time, the web between the score lines must be strong enough to withstand the forces of the component insertion machine without premature separation.

It is therefore necessary to establish statistical values for the force required to break apart the circuit boards along the pre-existing score lines and for the amount of flex experienced by the circuit boards during separation. Particularly, when a circuit board under test is clamped and broken along a score line, the circuit board should not flex more than 0.030 inch per inch of distance from the clamp (the overhang). In addition, the force required to break apart the circuit board along the score line should be between two and six pounds per lineal inch of score line with three pounds per lineal inch of score line being the nominal target value.

SUMMARY OF THE INVENTION

It is therefore an object of the present invention to provide a test fixture for measuring the force required to break apart a circuit board along a pre-existing score line and to measure the resulting flex at the time the break occurs.

It is likewise an object of the present invention to provide a method for testing a printed circuit board wth a pre-existing score line to determine the amount of force required to break the board along the score line and the flex that results at the time the circuit board breaks along the score line.

It is further an object of the present invention to provide a method for testing the force and flex involved in breaking a printed circuit board along a pre-existing score line in a repeatable fashion so that a statistical basis can be established for tracking the process for manufacturing printed circuit boards. The statistical tracking insures that a scored printed circuit board does not break apart prematurely during insertion of components on the board and that excessive force is not required to break apart the printed circuit board once it has been fully assembled.

The foregoing objectives are accomplished by a test fixture comprising a support surface for a circuit board to be tested, a clamp for holding the circuit board in place, an alignment target to locating the score line on the circuit board with respect to the clamp, a force gauge for exerting and measuring a downward force on the circuit board until the circuit board breaks along the score line, and a travel indicator for indicating the maximum flex experienced by the circuit board just prior to breaking.

From the force required to break the circuit board along the pre-existing score line and the maximum flex experienced just prior to breaking, a statistical basis can be established for the proper scoring depth and uniformity of the web of the circuit board. Particularly, if the force and flex data is outside the established norms, the web may be too thick or too thin, or there may be an excessive fillet in the bottom score line resulting from a dull cutter. Those problems are easily remedied before a production run is made to insure proper depth, fillet size, and uniformity of the printed circuit board score line. The proper depth, fillet, and uniformity of the score line insure that when a circuit board is broken apart along the pre-existing score line, the circuit board does not flex excessively thereby causing the components to lift and break free from the circuit board.

BRIEF DESCRIPTION OF THE DRAWINGS

FIG. 1 is a side elevation view of a printed circuit board test fixture in accordance with the present invention;

FIG. 2 is a top plan view of the printed circuit board test fixture in accordance with the present invention; and FIG. 3 is a front elevation view of the printed circuit board test fixture in accordance with the present invention.

DETAILED DESCRIPTION OF THE INVENTION

While the invention will be described in connection with a preferred embodiment and method, it will be understood that I do not intend to limit the invention to that embodiment or method. On the contrary, I intend to cover all alternatives, modifications, and equivalents as may be included within the spirit and scope of the invention as defined by the appended claims.

Turning to FIG. 1, there is shown a printed circuit board test fixture 10. The test fixture 10 comprises a base 12 with a support surface 14. Vertical members 16 extend upwardly from the support surface 14. A clamp bar 18 is slideably mounted for movement up and down along vertical members 16. The clamp bar can be frictionally secured to vertical members 16 at any point above the support surface 14.

A carriage 20 is likewise slideably mounted on the vertical support members 16. The carriage is urged upwardly along the vertical member 16 by means of springs 22. The carriage 20 is movable downward against the force of the springs 22 by means of a lever 24 secured to the vertical member 16 at pivots 26. The lever 24 engages the carriage 20 by means of roller bearings 28.

A force gauge 30 is fixed to the carriage 20 and movable therewith. The force gauge has a plunger 32 which extends vertically down from the carriage 20 toward the plane of the support surface 14. The plunger 32 terminates in a bearing bar 34 which engages a printed circuit board 36 which is under test for force and deflection. The force gauge 30 is Model No. FDK20-SR, manufactured by Wagner Instrument, Greenwhich, Conn.

A travel indicator 38 is mounted to the base 12 below the support surface 14. The travel indicator has a plunger 40 which extends upwardly toward the plane of the support surface 14 to engage the bottom of the circuit board 36 under test. The travel indicator 38 is Model No. C8IW/HD-64 MAG MAX HAND, manufactured by Federal Products, Corp., Providence, R. I.

An alignment target 42 is fixed to the clamp bar 18. The alignment target is an L-shaped member with a horizontal section 44 and a vertical section 46 at right angles. The vertical section 46 is spaced a distance 50 from the front edge 48 of the clamp bar 18. The vertical section 46 establishes a reference point from the front edge 48 of the clamp bar 18. The distance 50 from the front edge 48 of the clamp bar 18 to the vertical section 46 is defined as the overhang and is set at one inch.

In order to determine whether a particular circuit board will break at its score line within the specifications required for the automatic assembly and handling of printed circuit boards, the circuit board 36 with a score line 52 is placed on the support surface 14 and clamped beneath clamp bar 18 so that the score line 52 aligns vertically with the vertical section 46 of the alignment target 42. The plunger 40 of the travel indicator 38 is aligned closely adjacent to the score line and on the side of the score line adjacent the clamp bar 18 (to the left of the score line as shown in FIG. 1). Once the circuit board 36 has been secured by the clamp bar 18 with the score line in alignment with the alignment target 42, the operator pulls down on lever 24 so that the carriage 20 moves downwardly against the force of springs 22. Once the bearing bar 34 of the force gauge 30 engages the circuit board 36, the increasing force against the circuit board is recorded by the force gauge 30 as the carriage moves further downward. As the force gauge 30 exerts downward force on the circuit board 36, the circuit board is deflected downwardly, and that deflection is measured by the travel indicator 38.

At the instant the circuit board breaks along the score line 52, the maximum force on force gauge 30 is recorded and the maximum deflection on travel indicator 38 is recorded. The recorded force is normalized by dividing the force by the length 54 of the score line 52 to produce a number having units of pounds per lineal inch of score line length. Likewise, the deflection is normalized by dividing the travel recorded by the overhang distance 50 to produce a number having units of inches per inch of overhang.

As previously stated, it has been found that the maximum allowed deflection is 0.030 inch per inch overhang and the nominal value for the break force is three pounds per lineal inch of score line length. The break force, however, may range from about two to six pounds per lineal inch of score line length. Readings below two pounds per inch indicate that the web created by the score line is so weak that the boards may actually separate prematurely during the assembly process while components are being inserted or soldered. Alternatively, if the force is greater than six pounds per lineal inch of score line length, the additional force will cause excessive flexing with the possibility of dislodging circuit components when the circuit boards are broken apart.

I claim:

1. A printed circuit board test fixture for determining the breaking force for and deflection of a printed circuit board when the printed circuit board is broken along pre-existing score lines, the test fixture comprising:
   a. frame means;
   b. means for clamping the printed circuit board under test to the frame in an initial position;
   c. target means attached to the frame for locating the score line on the printed circuit board with respect to the clamp means;
   d. force exerting means attached to the frame and operable to exert a force on the circuit board to produce a deflection of the circuit board from the initial position to a final position at which final position the printed circuit board breaks at the score line;
   e. force measuring means associated with the force exerting means for measuring the deflecting force exerted on the printed circuit board; and
   f. deflection measuring means that measures the deflection of the printed board from its initial position to its final position.

2. A method of measuring the breaking force for and deflection of a printed circuit board when the printed circuit board is broken along pre-existing score lines, the method comprising the steps of:
   a. clamping the printed circuit board under test in an initial position;
   b. establishing a reference for locating the score line on the printed circuit board;
   c. exerting a deflecting force on the printed circuit board until the printed circuit board breaks along the score lines at a final position;
   d. measuring the amount of force required to break the printed circuit board along the score lines;
   e. measuring the amount of deflection of the printed circuit board from its initial position to its final position.

* * * * *